United States Patent
Petitdidier et al.

(10) Patent No.: US 10,718,709 B2
(45) Date of Patent: Jul. 21, 2020

(54) DEVICE FOR MEASURING RADIATION BACKSCATTERED BY A SAMPLE AND MEASUREMENT METHOD USING SUCH A DEVICE

(71) Applicant: Commissariat a l'energie atomique et aux energies alternatives, Paris (FR)

(72) Inventors: Nils Petitdidier, Grenoble (FR);
Selimen Benahmed, Grenoble (FR);
Anne Koenig, Saint Martin d'Uriage (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 6 days.

(21) Appl. No.: 16/227,458

(22) Filed: Dec. 20, 2018

(65) Prior Publication Data

US 2019/0195790 A1    Jun. 27, 2019

(30) Foreign Application Priority Data

Dec. 22, 2017    (FR) .................................. 17 63097

(51) Int. Cl.
G01N 21/47    (2006.01)
A61B 5/00    (2006.01)
G02B 6/08    (2006.01)

(52) U.S. Cl.
CPC ......... G01N 21/474 (2013.01); A61B 5/0075 (2013.01); A61B 5/441 (2013.01);
(Continued)

(58) Field of Classification Search
CPC ......... G01N 21/474; G01N 2021/4709; G01N 2021/4745; G01N 2021/4747;
(Continued)

(56) References Cited

U.S. PATENT DOCUMENTS 3,327,584 A * 6/1967 Kissinger ............. G01B 11/026
356/614
3,709,612 A * 1/1973 Clemens ............. G01N 21/474
356/407

(Continued)

FOREIGN PATENT DOCUMENTS

EP    2 743 743 A1    6/2014
EP    3 236 241 A1    10/2017
(Continued)

OTHER PUBLICATIONS

French Preliminary Search Report dated May 29, 2018 in French Application 17 63097, filed on Dec. 22, 2017 (with English Translation of Categories of Cited Documents & Written Opinion).

(Continued)

*Primary Examiner* — Roy M Punnoose
(74) *Attorney, Agent, or Firm* — Oblon, McClelland, Maier & Neustadt, L.L.P.

(57) ABSTRACT

A device for measuring radiation backscattered by a sample including:
- at least one light source that is configured to emit a light beam, along an axis of incidence, towards a surface of the sample so as to form, on said surface, an elementary illumination zone;
- an image sensor for forming an image of the radiation backscattered by the sample when the latter is illuminated by the light source, the image sensor lying in a detection plane;
- a bundle of optical fibres, extending, along an extension axis, between a proximal surface and a distal surface, the proximal surface being applied against the image sensor, the distal surface being configured to be applied against the surface of the sample;

(Continued)

wherein the light source is arranged around the bundle of optical fibres, and wherein the distance between the light source and the bundle of optical fibres is less than 1 mm.

12 Claims, 5 Drawing Sheets

(52) U.S. Cl.
CPC ....... *G02B 6/08* (2013.01); *G01N 2021/4709* (2013.01); *G01N 2021/4745* (2013.01); *G01N 2021/4747* (2013.01); *G01N 2201/0626* (2013.01)

(58) Field of Classification Search
CPC .......... G01N 2201/0626; A61B 5/0075; A61B 5/441; G02B 6/08
USPC .................................................. 356/342, 445
See application file for complete search history.

(56) References Cited

U.S. PATENT DOCUMENTS

| | | | | |
|---|---|---|---|---|
| 4,707,075 | A * | 11/1987 | Fukushima | ............ G02B 23/26 385/117 |
| 5,701,181 | A * | 12/1997 | Boiarski | .............. G01N 21/474 250/227.2 |
| 5,701,902 | A | 12/1997 | Vari et al. | |
| 2014/0152789 | A1 * | 6/2014 | Hu | ..................... G02B 23/2469 348/65 |
| 2016/0228047 | A1 * | 8/2016 | Roig | ..................... G01N 21/474 |
| 2016/0235303 | A1 | 8/2016 | Fleming et al. | |
| 2017/0307524 | A1 | 10/2017 | Sorgato et al. | |
| 2018/0132708 | A1 | 5/2018 | Rizo | |

FOREIGN PATENT DOCUMENTS

| | | |
|---|---|---|
| WO | WO 96/08201 A1 | 3/1996 |
| WO | WO 2016/181077 A1 | 11/2016 |

OTHER PUBLICATIONS

Petitdidier, N., et al. "Development of a wearable CMOS-based contact imaging system for real-time skin condition diagnosis", Progress in Biomedical Optics and Imaging, SPIE—International Society for Optical Engineering, vol. 10412, 2017, 5 pages.

Koenig, A., et al. "Diffuse Reflectance Spectroscopy: A clinical study of tuberculin skin tests reading", Proceedings of SPIE, vol. 8592, 2013, 8 pages.

Nichols, B., et al. "A Quantitative Diffuse Reflectance Imaging (QDRI) System for Comprehensive Surveillance of the Morphological Landscape in Breast Tumor Margins", PLoS ONE 10(6), 2015, 25 pages.

European Search Report dated Feb. 27, 2019 in European Patent Application No. 18214247.1, (with English translation of Categories of Cited Documents), citing document AA therein, 14 pages.

* cited by examiner

DEVICE FOR MEASURING RADIATION BACKSCATTERED BY A SAMPLE AND MEASUREMENT METHOD USING SUCH A DEVICE

TECHNICAL FIELD

Diffuse reflectance spectrometry, often referred to by the acronym DRS, consists in utilizing the light backscattered by a scattering object subjected to, generally pointlike, illumination. This technique proves to be efficacious for characterizing optical properties of objects, in particular the scattering or absorption properties.

Implemented on the skin, this technique makes it possible for example to characterize the skin, as disclosed in EP2762064. The authors of this document describe a measurement probe intended to be applied against the skin. This probe comprises a central optical fibre, termed the excitation fibre, intended to direct a light beam onto a skin sample. Optical fibres, termed detection fibres, arranged around the central fibre, gather an optical signal backscattered by the skin. Means for spectrally analysing the optical signal thus collected, coupled with calculation algorithms, make it possible to estimate parameters of the dermis, in particular the concentration of certain chromophores, for example oxyhaemoglobin or deoxyhaemoglobin, and also parameters governing the path of the photons through the dermis, in particular the reduced scattering coefficient $\mu_s'$ and the absorption coefficient $\mu_a$. The applications are numerous, and may for example make it possible to detect and to quantify concentrations of elements in the skin, or to access information relating to the oximetry of the blood vessels in the skin. Applications are described in EP2762064, as well as in the publication by Haahr R., "An Electronic Patch for Wearable Health Monitoring by Reflectance Pulse Oxymetry", IEEE Transactions on biomedical circuits and systems, 2011, or else in U.S. Pat. No. 805,532.

According to the principles of the scattering of light in a scattering medium, the mean depth of penetration of the photons into a scattering object increases with the separation between the excitation fibre and the detection fibre. Stated otherwise, the more the distance between the excitation fibre and the detection fibre increases, the more the result is representative of the optical properties of the deep layers of the examined medium. Conversely, the more this distance decreases, the more the result is representative of the surface layers of the scattering medium.

Now, in order to perform a sufficiently sensitive measurement, each fibre has a diameter equal to a few hundreds of microns, typically 500 µm for the excitation fibre and 150 µm for each detection fibre. Moreover, because of manufacturing constraints, it is hardly conceivable to significantly reduce the distance between these fibres. It follows from this that the minimum separation between each fibre cannot be less than a threshold value, generally of the order of a few hundred µm, and generally greater than 300 µm.

Therefore, whereas the device disclosed in EP2762064 is suitable for characterizing the dermis, it are not able to characterize the epidermis, the latter extending, depending on the individual and the body zone, over the first 100 to 300 microns of the skin.

EP3054281 discloses a device allowing this problem to be overcome by arranging an optical system between optical fibres and an object to be characterized, for example the skin of an individual. According to this device, the optical fibres are arranged at a distance away from the object to be characterized, and an optical system, having a magnification of greater than one, is arranged between the fibres and the object to be characterized. The optical system provides optical coupling between the optical fibres and the surface of the characterized object. Such a device offers good performance, but it is too bulky to be worn continuously by a person. This device is suitable more for examinations conducted on an occasional basis than for continuous tracking using a wearable device. Additionally, the cost of such a device is relatively high.

The invention is an alternative to the device disclosed in EP3054281. The invention allows a scattering object, in particular the optical properties of the surface layer of a sample, to be characterized by highly compact means of simple design.

DISCLOSURE OF THE INVENTION

A first subject of the invention is a device for measuring backscattered radiation for measuring radiation backscattered by a sample including:
  at least one light source that is configured to emit a light beam, along an axis of incidence, towards a surface of the sample so as to form, on said surface, an elementary illumination zone;
  an image sensor for forming an image of the radiation backscattered by the sample when the latter is illuminated by the light source, the image sensor lying in a detection plane;
  a bundle of optical fibres, extending, along an extension axis, between a proximal surface and a distal surface, the proximal surface being applied against the image sensor, the distal surface being configured to be applied against the surface of the sample;

The light source is preferably arranged at a distance of less than 1 mm away from the bundle of optical fibres.

The light source may be arranged against the bundle of optical fibres.

The device may include one or more of the following features, taken alone or in combination:
  the light source is arranged at the periphery of the bundle of optical fibres, between the image sensor and the sample;
  the light source is flush with the distal surface;
  the axis of incidence and the axis of extension may form an angle of between 10° and 70° or 80°;
  the extension axis is perpendicular to the detection plane.
  The optical fibres of the bundle of optical fibres:
    are oriented in parallel to the extension axis;
    or form a bundle diverging or converging away from/toward the image sensor;
  The device includes a plurality of light sources, each light source being arranged around the bundle of optical fibres. At least two light sources emit light beams in different spectral bands, respectively.
  At least one light source is such that the axis of incidence of the light beam produced by the latter intersects the extension axis of the bundle of optical fibres.
  At least one light source is:
    a light-emitting diode;
    or a laser diode;
    or an end of an optical fibre, referred to as the illuminating optical fibre, the illuminating optical fibre being coupled to a light source.
  The image sensor includes a matrix-array of pixels, such that the distance, in the detection plane, between at least one light source and the matrix-array of pixels is less than 1 mm or less than 500 µm; this is the distance, parallel to the detection plane, between the incident beam produced by the light source and the matrix-array of pixels.

The image sensor, the bundle of optical fibres and each light source are held securely to one another by means of a holding support.

Another object of the invention is a method for estimating a scattering and/or absorption optical property of a sample using a device according to the first object of the invention, the method including:

a) illuminating the sample using the light source of the device so as to form, on a surface of the sample, an elementary illumination zone;

b) forming, using the image sensor, an image representing radiation backscattered by the sample under the effect of the illumination, the backscattered radiation emanating from the surface of the sample outside of the elementary illumination zone at several distances, referred to as backscattering distances, away from the elementary illumination zone;

c) determining a scattering and/or absorption optical property according to an intensity of the backscattered radiation, at various backscattering distances, at least one backscattering distance being less than 1 mm or than 500 μm.

Other advantages and features will become more clearly apparent from the following description of particular embodiments of the invention, which are provided by way of nonlimiting examples, and which are shown in the figures listed below.

FIGURES

FIGS. 2A and 2B collate results of experimental measurements carried out on calibration samples, the optical properties of which are known, using devices according to the configurations presented in conjunction with FIGS. 1A and 1C.

FIGS. 4A and 4B collate results of experimental measurements carried out on calibration samples, the optical properties of which are known, using devices according to the configurations presented in conjunction with FIGS. 1A, 1C and 3A.

DISCLOSURE OF PARTICULAR EMBODIMENTS

The term "optical scattering or absorption property" is understood to mean an absorption coefficient, a scattering coefficient, or a reduced scattering coefficient, these quantities being known to a person skilled in the art and described in application EP3054281, the latter being included as a reference. On the basis of absorption properties, it is possible to determine a concentration of a component of the sample. For example, when the sample is the skin of a human or of an another animal, it is possible to determine a concentration of various components of the skin, as well as of the oxyhaemoglobin or of the deoxyhaemoglobin of the blood flowing through the skin. For example, considering the absorption coefficient $\mu_a$, it is possible to use an expression such that:

$$\mu_a = f(\Sigma_i \varepsilon_i c_i) \text{ where}$$

$c_i$ is a concentration of components i in the skin (in mol·L$^{-1}$), $\varepsilon_i$ is an extinction coefficient of each component i (in L·mol$^{-1}$·cm$^{-1}$);

$f$ is a function relating $c_i$ and $\varepsilon_i$ to $\mu_a$.

The term "a" or "one" is to be understood to mean "at least one".

Figures 1A, 1B:
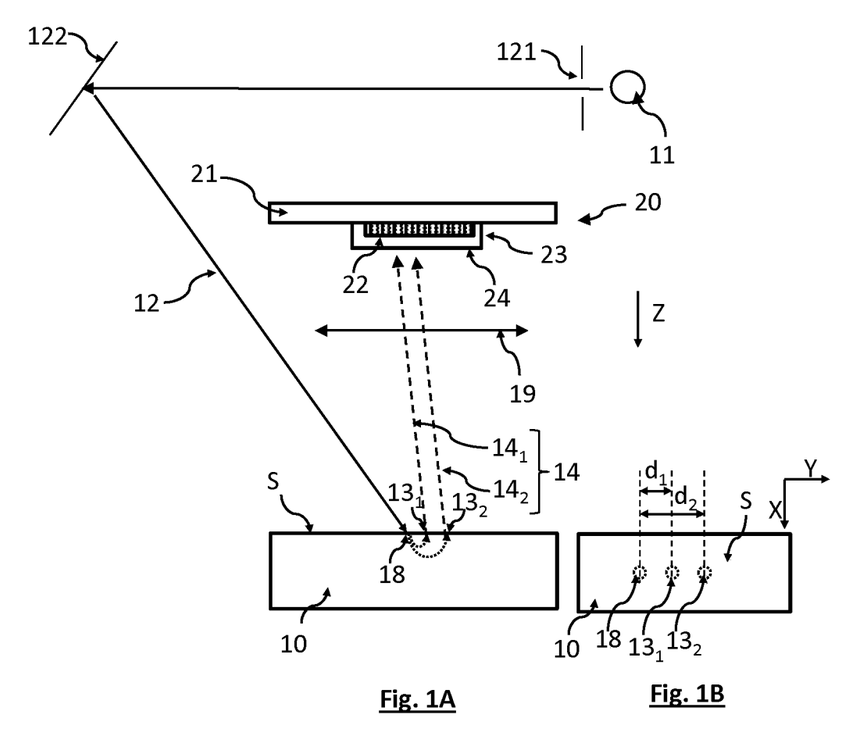
FIGS. 1A and 1B show a device according to a configuration known from the prior art, termed the "remote" configuration.

FIG. 1A shows a configuration of the prior art, termed the "remote" configuration, according to which a light source 11 emits an illuminating beam 12 in a spectral band $\Delta\lambda$, so as to illuminate a sample 10 to be characterized. The sample lies along a surface S. The illuminating beam 12 passes through an aperture 121, and is then reflected towards the sample 10 by a reflecting element 122. It reaches the surface of the sample at an oblique incidence. The illuminating beam 12 forms, on the surface of the sample, a luminous trace, referred to as the elementary illumination zone 18. The elementary illumination zone corresponds to an intersection between the incident light beam 12 and the surface S of the sample. In the example shown, it is pointlike.

Under the effect of the illumination, a portion of the light from the illuminating beam 12 scatters through the sample, and is backscattered thereby so as to form backscattered radiation 14 emanating from the surface S of the sample. The latter propagates towards an optical system 19 that is optically coupled to an image sensor 20. The surface of the sample then lies in an object focal plane of the optical system 19. Thus, the optical system 19 conveys the image of the backscattering radiation 14, emanating from the surface of the sample S, to the image sensor 20. Such a device is an application of the patent application EP3054281 cited in the prior art.

The image sensor 20 may in particular be a CMOS or CCD sensor. It includes a carrier 21, including for example a readout circuit, on which a matrix-array of pixels 22 is arranged, confined within a protective enclosure 23. The matrix-array of pixels 22 lies in a detection plane P. The protective enclosure 23 includes a transparent window 24, lying parallel to the matrix-array of pixels 22. The term "transparent" is understood to mean transparent in the spectral band $\Delta\lambda$. Numerous electrical connections lie in the protective enclosure 23. In a plane parallel to the detection plane P, the protective enclosure extends over a thickness of 2 or 3 mm around the matrix-array of pixels 22.

The path of photons scattering through the sample 10 to form the backscattered radiation 14 is schematically shown by dotted arrows. The backscattered radiation 14 emanates from the surface S of the sample 10 in various distinct elementary backscattering zones of the elementary illumination zone 18. The term "backscattering distance" refers to a distance separating an elementary backscattering zone from the elementary illumination zone 18. FIG. 1B is a view from above of the surface of the sample. FIGS. 1A and 1B show two elementary backscattering zones $13_1$ and $13_2$ lying at two backscattering distances $d_1$ and $d_2$, respectively, away from the elementary illumination zone 18, and from which emanate backscattered radiation $14_1$ and backscattered radiation $14_2$. The term "elementary backscattering zone" refers to a zone of the surface of the sample whose size is such that the zone may be considered to be located the same distance away from the elementary illumination zone 18. An elementary backscattering zone may be pointlike. The area of a backscattering zone is then smaller than 1 mm$^2$, or even smaller than 100 µm$^2$. An elementary backscattering zone may also describe all or part of a thin ring, the thickness of which is preferably less than 1 mm, or even less than 500 µm, or even 100 µm or 50 µm, extending around the elementary illumination zone 18.

As mentioned in EP3054281, the more the backscattering distance decreases, the more the depth of the path of the photons forming the backscattered radiation through the sample decreases. Thus, the more the backscattering distance decreases, the more the backscattered radiation is representative of a surface portion of the sample. Conversely, the more the backscattering distance increases, the more the backscattered radiation is representative of a deep portion of the sample.

By means of the optical system 19, each pixel of the matrix-array of pixels 22 is optically coupled to an elementary backscattering zone. It is understood that this device makes it possible to detect radiation backscattered over small backscattering distances, typically of a few tens of microns, thereby making it possible to correctly analyse the portion of the sample closest to the surface, extending a few tens of microns below the surface S. However, the device is bulky. It is not suitable for portable use, being worn by a human or another animal.

Figure 1C:
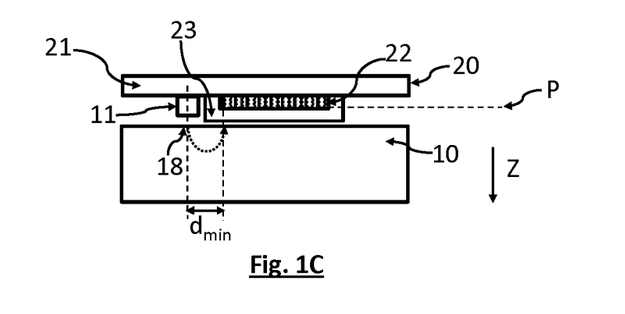
FIG. 1C schematically shows a device according to a contact configuration, of simple design.

The inventors have tested a substantially more compact configuration shown in FIG. 1C. It includes an image sensor 20, similar to the sensor described in conjunction with FIG. 1A. A point light source 11, for example a light-emitting diode, is arranged on the carrier of the image sensor 21. The image sensor 20 is applied directly against the sample 10. However, in such a configuration, the distance, parallel to the surface S of the sample, between the centre of the light source 11 and the matrix-array of pixels 22, may not be less than 3 or 4 mm. This is due to the dimensions of the protective enclosure 23 extending around the matrix-array of pixels 22. Because of this, in such a configuration, the backscattering distance cannot be less than a minimum distance $d_{min}$, here equal to 4 mm, which makes determining the scattering and/or absorption optical properties of the portion of the sample closest to the surface thereof inconceivable. Moreover, even when the optical properties of the sample are uniform, such a distance proves to be too great for correctly characterizing the scattering and/or absorption properties of the sample, as explained below.

The inventors have conducted experimental tests with a view to comparing the performance of the configurations shown in FIGS. 1A and 1C, respectively. To achieve this, they used calibration samples taking the form of phantoms, the scattering and absorption optical properties of which are known. For the tests, the following components were used:

Light source 10 for the "remote" configuration of FIG. 1A: Power Technologies Inc. laser diode with wavelength λ=690 nm.

Light source 10 for the "contact" configuration of FIG. 1C: Light-emitting diode (Kingbright KPTD-1608SURK) emitting in a spectral band centred on a wavelength of λ=640 nm and having an angle of emission of about 60°.

Image sensor 20: UI-1492-LE CMOS sensor by IDS Imaging.

In the remote configuration, the optical system 19 is a Xenoplan 1.4/23-0902 objective—23 mm by Schneider Kreuznach, arranged at a distance of 90 mm away from surface of the sample. An optical density, producing an attenuation of 10-2, was arranged between the laser and the mirror 122. Two polarizing filters are also arranged between the light source 11 and the sample 10 and between the sample 10 and the sensor 20, respectively. The optical density and the polarizing filters are optional and are not shown in FIG. 1A. The polarizing filters make it possible to prevent the diffuse reflection of the incident beam 12 off the surface of the sample reaching the image sensor 20.

Various calibration samples were used, these having one and the same reduced scattering coefficient $\mu_s'$ and various absorption coefficients pa. During each test, the scattering and absorption coefficients were determined according to the method described in EP3054281, In general, the coefficients $(\mu_a, \mu_s')$ are obtained by comparison between:
- a reflectance measured at various backscattering distances;
- a reflectance that is modelled, at each backscattering distance, by taking into account various reduced scattering coefficients $\mu_s'$ and various absorption coefficients $\mu_a$.

The pair $(\mu_a, \mu_s')$ is then determined, which pair best corresponds to the reflectance measured at the various backscattering distances.

The diffuse reflectance corresponds to an intensity of detected backscattering radiation normalized by the intensity of the light beam incident on the sample, and may be assigned corrective factors, taking into account the response of the components used, for example the image sensor, the optical components or the light source.

The remote configuration was first implemented, and the pair $(\mu_a, \mu_s')$ was determined for six calibration samples on the basis of the backscattered signal at various backscattering distances, comprised between 500 µm and 5 mm, according to a sampling interval of 80 µm. The results of this test are represented by a dot in FIGS. 2A and 2B.

Figure 2A:
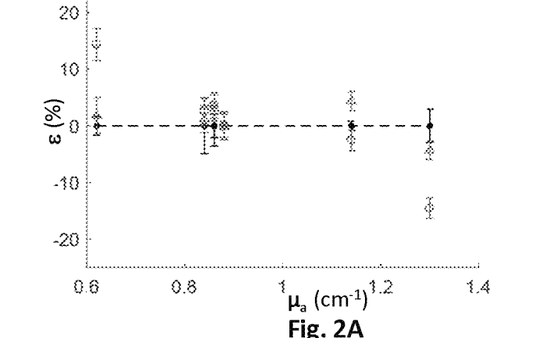
FIG. 2A shows a relative quantization error of an absorption coefficient according to the absorption coefficient of the calibration sample.
Figure 2B:
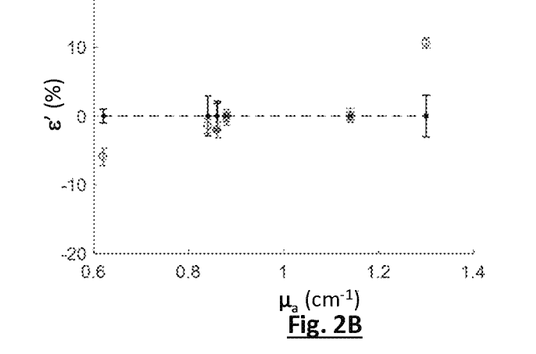
FIG. 2B shows a relative quantization error of a reduced scattering coefficient according to the absorption coefficient of the calibration sample.

FIG. 2A shows the relative error £ affecting the determination of the absorption coefficient $\mu_a$ (ordinate axis) as a function of the actual absorption coefficient $\mu_a$ of each sample (abscissa axis). FIG. 2B shows the relative error ε' affecting the determination of the reduced scattering coefficient $\mu_s'$ (ordinate axis) as a function of the actual absorption coefficient $\mu_a$ of each sample (abscissa axis).

The contact configuration was implemented based on an assumption regarding the value of the reduced scattering coefficient $\mu_s'$. The absorption coefficients $\mu_a$ for each calibration sample were thus determined. The results of this test are represented by a triangle in FIG. 2A.

The contact configuration was implemented without any assumption regarding the value of the reduced scattering coefficient $\mu_s'$. The absorption and reduced scattering coefficients $(\mu_a, \mu_s')$ for each calibration sample were thus determined. The results of this test are represented by a circle in FIGS. 2A and 2B.

The following conclusions are drawn from the results presented in FIGS. 2A and 2B:
- the remote configuration provides optimal performance and may be considered a reference method;
- the contact configuration with an assumption regarding the reduced scattering coefficient provides an acceptable estimate for the absorption coefficient (cf. FIG. 2A), with an error range less than or of the order of ±5%;
- the contact configuration without an assumption regarding the reduced scattering coefficient may result in a substantial measurement error, possibly reaching ±15%, affecting the determination of the absorption (FIG. 2A) and reduced scattering (FIG. 2B) coefficients. Moreover, the errors respectively affecting these two coefficients appear to be correlated in terms of absolute value.

Figure 2C:
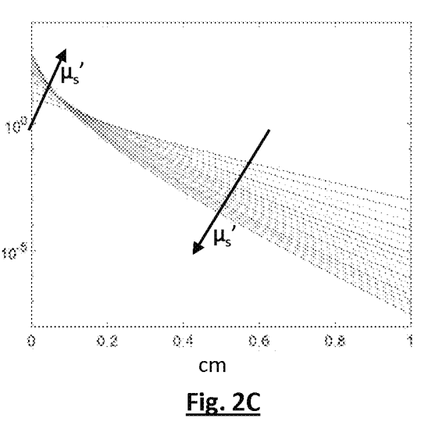
FIG. 2C shows a variation in the reflectance of a tissue according to the backscattering distance for various values of the reduced scattering coefficient.
Figure 2D:
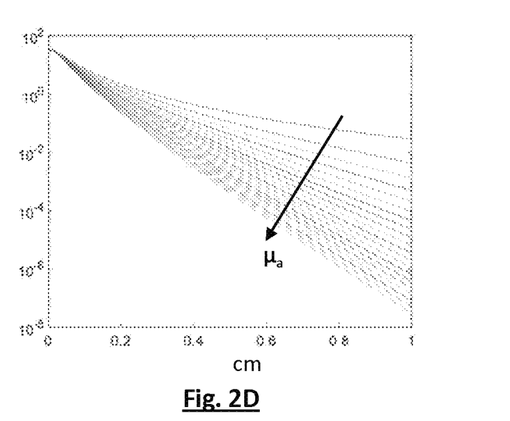
FIG. 2D shows a variation in the reflectance of a tissue according to the backscattering distance for various values of the absorption coefficient.

The inventors have attributed the poorer performance of the contact configuration to the fact that when the minimum backscattering distance ($d_{min}$) is small, typically less than 1 mm, the reflectance mainly varies according to the reduced scattering coefficient. FIGS. 2C and 2D illustrate this observation. These figures respectively show the variation in the reflectance (ordinate axis) according to the backscattering distance (abscissa axis) while considering various reduced scattering coefficients $\mu_s'$ and various absorption coefficients $\mu_a$, respectively. These reflectance values were obtained by modeling the scattering equation. In these two figures, the arrows represent increasing values of the coefficients $\mu_a$ (in FIG. 2D) and $\mu_s'$ (in FIG. 2C).

FIG. 2C was obtained by varying $\mu_s'$ from 10 $cm^{-1}$ to 80 $cm^{-1}$ by intervals of 4 $cm^{-1}$, the absorption coefficient $\mu_a$ of the modelled sample being set at 1 $cm^{-1}$. The refractive index of the sample is set at 1.33, the sample being placed in air, the refractive index of which is equal to 1. The anisotropy coefficient g is set at 0.8. The anisotropy coefficient, known to a person skilled in the art, relates the reduced scattering coefficient $\mu_s'$ to the scattering coefficient $\mu_s$ according to the expression:

$$\mu s' = \mu_s(1-g)$$

FIG. 2D was obtained by varying $\mu_a$ from 0.01 $cm^{-1}$ to 4 $cm^{-1}$ by intervals of 0.2 $cm^{-1}$, the absorption coefficient $\mu_s'$ of the modelled sample being set at 20 $cm^{-1}$. The refractive index of the sample is set at 1.33, the sample being placed in air, the refractive index of which is equal to 1. The anisotropy coefficient g is set at 0.8.

It is observed that when the backscattering distance is less than 1 mm, the reflectance hardly varies with $\mu_a$. Conversely, at small backscattering distances, the reflectance varies with $\mu_s'$. Beyond a backscattering distance of 1 mm, the intensity of the backscattered radiation decreases both with $\mu_a$ and with $\mu_s'$. Considering such a variation, it is therefore difficult to estimate both the absorption coefficient $\mu_a$ and the reduced scattering coefficient $\mu_s'$. Specifically, in the absence of a short-distance measurement, i.e. a measurement at a backscattering distance of less than 1 mm, it is difficult to simultaneously estimate the absorption $\mu_a$ and reduced scattering $\mu_s'$ coefficients, since the reflectance, i.e. the normalized intensity of the backscattered radiation, is affected in the same way by these two coefficients.

Figure 3A:
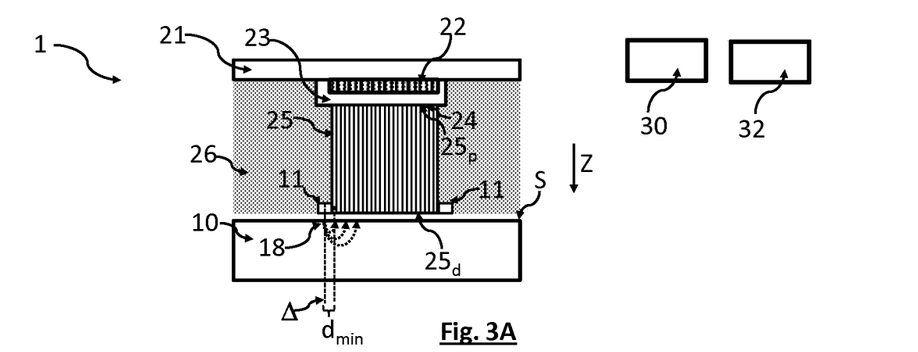
FIGS. 3A to 3G show various embodiments of a device according to the invention.

Having observed the above, in order to be able to satisfactorily estimate the absorption and scattering properties using a compact and wearable device, the inventors have designed a device such as shown in FIG. 3A. The device includes an image sensor 20 such as described above. It includes a light source 11, capable of producing an illuminating beam 12 propagating towards the sample. The intersection of the illuminating beam 12 with the surface S of the sample forms an elementary illumination zone 18. The elementary illumination zone may be pointlike, i.e. having an area of less than 5 $mm^2$, preferably less than 2 $mm^2$ or 1 $mm^2$. It may also form a pattern, the size of which is less than 5 mm, or even 2 mm or 1 mm. It may for example be a thin line. In FIG. 3A, the illuminating beam 12 is not shown because the device 1 is applied against the sample 10.

The light source 11 may for example emit the illuminating beam 12 in a spectral emission band Δλ lying in the visible or near-infrared portion of the spectrum, i.e. between 400 nm and 950 nm. Preferably, the bandwidth is less than 100 nm, or even less than 50 nm or 20 nm. The term "bandwidth" is understood to mean the full width at half-maximum of the spectral emission band.

In the example shown in FIG. 3A, the light source 11 is a light-emitting diode such as described in conjunction with the preceding examples. Alternatively, the light source may be a low-power laser diode. It may also be an end of an optical fibre, the optical fibre being coupled to a light source.

The device includes a bundle of optical fibres 25, also referred to as a fibre-optic plate. The bundle of optical fibres extends between a proximal surface $25_p$, arranged against the image sensor 20, and a distal surface $25_d$, which is intended to be applied against the sample 10 to be analysed. The bundle of optical fibres 25 includes a plurality of optical fibres that are joined to one another. The optical fibres are bonded to one another. The bundle of optical fibres may include several hundred, or even several thousand, optical fibres. They allow an image of the backscattered radiation 14 emanating from the surface S of the sample to be conveyed towards the matrix-array of pixels 22 of the image sensor 20. In this example, the optical fibres of the bundle 25 lie along an axis Z, referred to as the axis of extension, such that the bundle 25 allows the image formed on the surface of the tissue to be conveyed, along the axis of extension, towards the matrix-array of pixels 22. The bundle of optical fibres is preferably joined to the image sensor. The optical fibres of the bundle lie in parallel along the axis of extension Z, as described in conjunction with FIGS. 3A, 3C, 3D and 3G, or may be inclined with respect thereto, as described in conjunction with FIGS. 3E and 3F. When they are inclined with respect to the axis of extension, they may form a bundle diverging or converging away from/toward the image sensor 20. The proximal surface $25_p$ of the bundle lies parallel to the detection plane P, while the distal surface $25_d$ of the bundle lies parallel to the surface S of the sample. Preferably, the detection plane is parallel to the surface of the sample. This is particularly the case when the examined sample is deformable, when, by applying the device against the sample, the surface of the sample S lies parallel to the distal surface $25_d$ of the bundle. In this example, the proximal surface $25_p$ is bonded to the transparent window 24. In this example, the axis of extension Z of the bundle 25 is orthogonal to the detection plane P, which corresponds to a preferred configuration.

Through the use of the bundle 25 into all or part of the matrix-array of pixels 22, the optical fibres of the bundle of fibres open onto pixels that are adjacent to one another.

Preferably, the area of the proximal surface $25_p$ is smaller than or equal to the area of the matrix-array of pixels 22. Thus, in a transverse plane XY in which the proximal and distal surfaces lie, the beam 25 is inscribed within the perimeter defined by the matrix-array of pixels. This allows the light source 11 to be arranged against the bundle 25 so as to minimize the distance $d_{min}$, parallel to the surface S of the sample (or in the detection plane P), between the light source 11 and the matrix-array of pixels 22. Thus, the device makes it possible to detect a backscattered signal emanating from the surface of the sample S over a minimum backscattering distance $d_{min}$ that is shorter than that of the configuration described in conjunction with FIG. 1C. This distance corresponds to the shortest distance, parallel to the plane of the sample, between the light source 11 and the bundle of optical fibres 25. Preferably, the distance $d_{min}$ is shorter than 1 mm, and even more preferably shorter than 500 µm. It corresponds to a distance, parallel to the detection plane, between the axis of incidence Δ of the beam produced by the light source and the matrix-array of pixels 22. Using the bundle 25 of optical fibres, the area of which is smaller than or equal to the area of the matrix-array of pixels 22, allows the distance, parallel to the surface of the sample, or in the detection plane P, between the light source 11 and the pixels of the image sensor 20 to be significantly decreased.

It should be noted that using a bundle 25 of optical fibres allows the backscattered radiation of a sample to be analysed using a standard image sensor 20, without requiring the latter to be modified.

Depending on the desired spatial resolution to be obtained, the diameter of each fibre of the bundle may be between 5 µm and 100 µm or 200 µm, for example 70 µm. In order to decrease leakages of light between adjacent fibres, fibres of the bundle may advantageously be surrounded by an opaque material.

The light source 11 may be flush with the distal surface $25_d$ of the bundle of fibres 25, or be arranged set back with respect thereto, for example by a distance of less than 1 cm, or even less than 5 mm. Bringing the light source 11 close to the distal surface 25 makes it possible to limit the area of the elementary illumination zone 18, due to the divergence of the incident light beam 12.

The distal surface $25_d$ of the bundle 25 may be coated with a transparent biocompatible material, facilitating use of the device on the skin of a human or of another animal.

The inventors have used a bundle of optical fibres of 70 µm in diameter, with a numerical aperture of 0.84, supplied by Paradigm Optics, reference PA0470, having a diameter of 1 inch in the plane XY and a thickness of ½ inch along the axis Z. This has allowed a minimum backscattering distance $d_{min}$ equal to 470 µm to be obtained.

The image sensor 20, the light source 11 and the bundle 25 may be held securely by a holding support 26, the latter possibly being an encapsulation material made of rigid plastic.

Figure 3B:
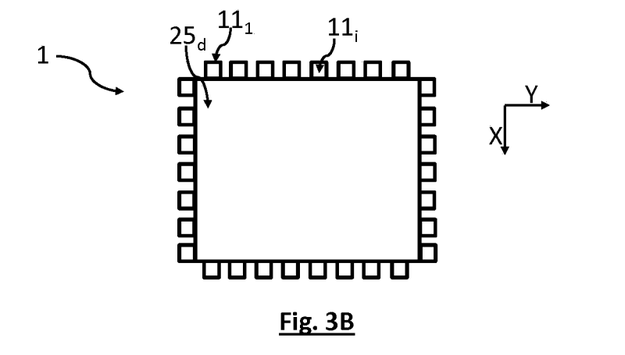
Figure 3C:
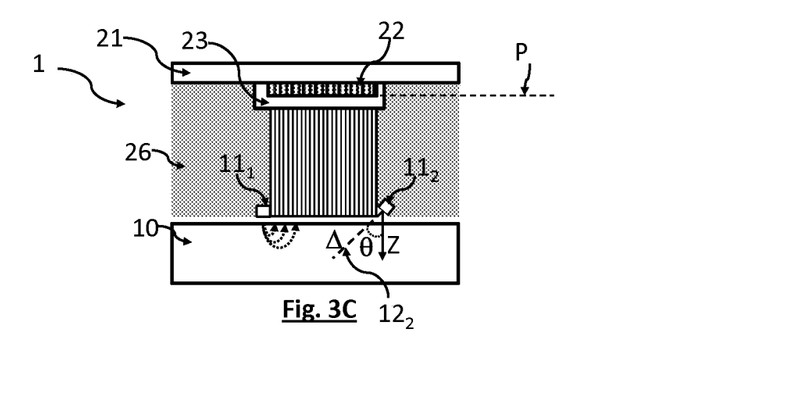

According to the examples shown in FIGS. 3A, 3B and 3C, the device includes a plurality of light sources 11. FIG. 3B shows various light sources $11_1$ . . . $11_i$ . . . arranged around a bundle of optical fibres 25, at the smallest possible distance away therefrom, this distance being for example smaller than 1 cm or than 1 mm. Light sources emitting in spectral bands Δλ differing from one another may then be used. This allows the optical properties of the object to be characterized in the various spectral bands used. Preferably, the spectral bandwidth of each light source is less than 100 nm, less than 50 nm or less than 20 nm. The term "bandwidth" is understood to mean the full width at half-maximum of the emission peak corresponding to the spectral band.

In FIGS. 3A and 3C, the optical fibres are parallel to the axis of extension Z.

Each light source is preferably included within the holding support, such that the device forms a one-piece part.

According to one embodiment, shown in FIG. 3C, the device includes a light source 11 emitting an incident beam 12 propagating along an axis of incidence Δ that is inclined with respect to the axis of extension Z along which the incident bundle 25 lies. The angle of inclination θ between the axis of incidence Δ and the axis of extension Z may for example be between 10° and 70° to 80°. It is preferably between 30° and 45°. This allows the elementary illumination zone 18 to be brought closer to the matrix-array of pixels 22 in the plane defined by the surface of the sample. The angle of inclination may for example be 35°.

Figure 3D:
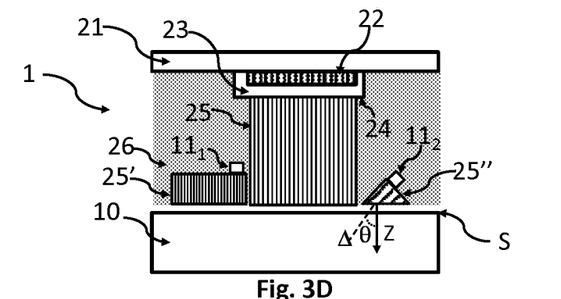

According to one embodiment, shown in FIG. 3D, the device includes a first light source $11_1$ that is optically coupled to an auxiliary bundle 25' of optical fibres 25', extending between the first light source $11_1$ and a surface of the holding support 26 that is intended to be applied against the surface of the sample 10. Optionally, the device includes a second light source $11_2$ that is optically coupled to a second auxiliary bundle 25'' of auxiliary optical fibres. The latter is configured to direct the light produced by the second light source $11_2$ along an axis of incidence Δ forming an angle of inclination θ with the axis of extension Z. As described in conjunction with FIG. 3C, the angle of inclination may be between 10° and 70° or 80°. It is preferably between 30° and 45°.

Figure 3E:
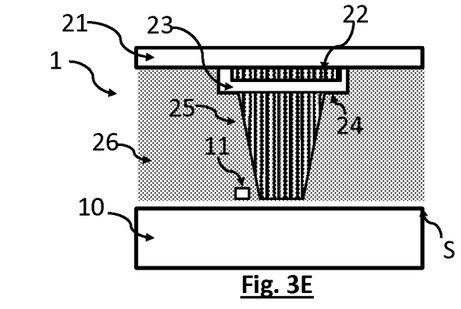
Figure 3F:
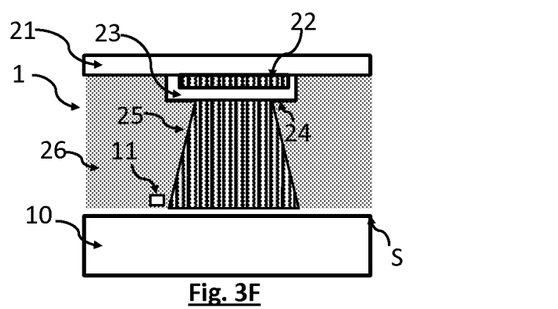

According to embodiments shown in FIGS. 3E and 3F, the fibres of the bundle of optical fibres 25 are not all oriented parallel to the axis of extension Z. These optical fibres form a bundle converging around the axis of extension Z. In FIG. 3E, the bundle 25 converges towards the surface of the sample. This allows the backscattering distances to be brought closer to one another. In FIG. 3F, the bundle 25 diverges away from the image sensor, allowing sensitivity to be increased, since several fibres may thus be coupled to one and the same pixel of the image sensor.

Figure 3G:
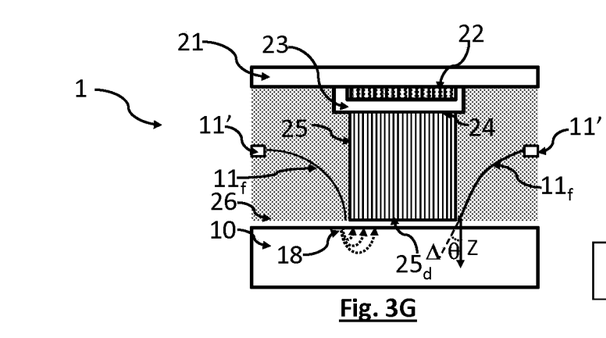

According to one embodiment, shown in FIG. 3G, at least one light source is fibre based, in the sense that an illuminating optical fibre $11_f$ extends from the light source towards the sample. A light source 11', included within the holding support 26, and from which an illuminating fibre $11_f$ extends to a surface of the holding support that is capable of being applied against the sample 10, is shown. Another light source 11', included within the holding support 26, and from which an illuminating fibre $11_f$ extends to a surface of the holding support that is capable of being applied against the sample 10, such that an illuminating beam is propagated along an axis of incidence Δ forming an angle of inclination θ with respect to the axis of extension Z, is also shown. The angle of inclination is similar to that described in conjunction with FIG. 3C or 3D. The end of the illuminating fibre $11_f$ then forms the light source 11. The use of a fibre allows the light source to be brought closer to the bundle of optical fibres 25.

Figure 3H:
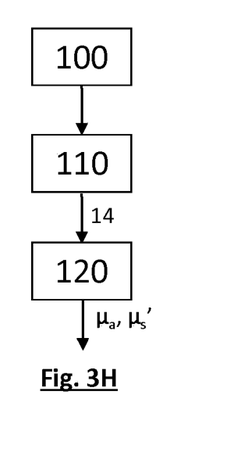
FIG. 3H illustrates the main steps of a method for determining optical properties of the invention using a device such as shown in FIGS. 3A to 3C.

The device may be connected to a processor 30, including a memory 32, in which instructions making it possible to determine the absorption and/or scattering optical properties on the basis of the backscattered radiation detected, over various backscattering distances, by the image sensor 20 are stored. The method may include the following steps, illustrated in FIG. 3H:

Step 100: applying the device against the sample, in contact therewith. Preferably, after application, the surface S of the sample lies parallel to the distal surface $25_d$ of the bundle 25.

Step 110: illuminating the sample using the light source or the light sources and detecting radiation 14 backscattered by the sample over at least two different and nonzero backscattering distances.

Step 120: on the basis of the backscattered radiation detected by the image sensor, estimating, using the processor 30, scattering and/or absorption optical properties on the basis of algorithms. The algorithms used are for example based on a comparison between measured intensity values of the backscattered radiation and values modelled by considering various optical property values, as described in EP3054281. Advantage is then taken of the fact that at least one backscattering distance under consideration is shorter than 1 mm, or even shorter than 500 µm, which makes it possible to better estimate the optical properties.

The device shown in FIG. 3A was used with a single light source, corresponding to the light-emitting diode described in conjunction with the above tests. The device was used on calibration samples in a similar manner to that in the tests described in conjunction with FIGS. 2A and 2B.

Figure 4A:
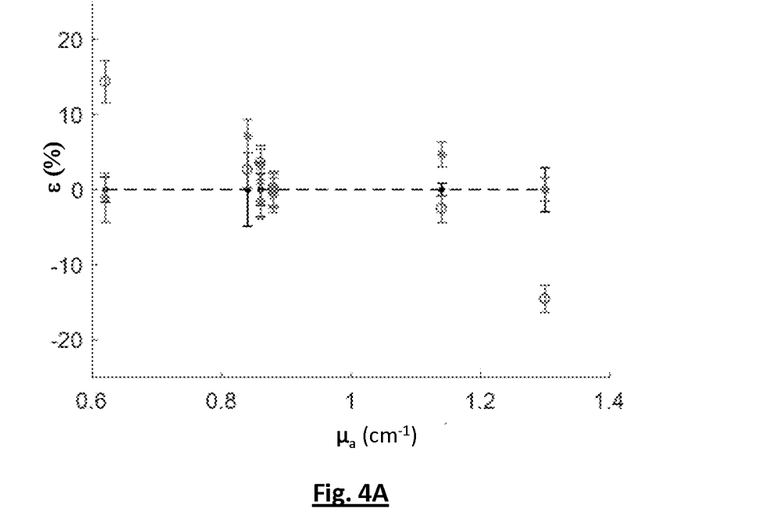
FIG. 4A shows a relative quantization error of an absorption coefficient according to the absorption coefficient of the calibration sample.

FIG. 4A shows the relative error ε affecting the determination of the absorption coefficient $\mu_a$ (ordinate axis) as a function of the actual absorption coefficient $\mu_a$ of each sample (abscissa axis). This figure shows:

- the results implementing the remote configuration such as shown in FIG. 1A, these results corresponding to the points in the form of dark dots;
- the results implementing the contact configuration such as shown in FIG. 1C, these results corresponding to the points in the form of circles;
- the results implementing the configuration according to the invention, such as shown in FIG. 3A, these results corresponding to the points in the form of asterisks.

Figure 4B:
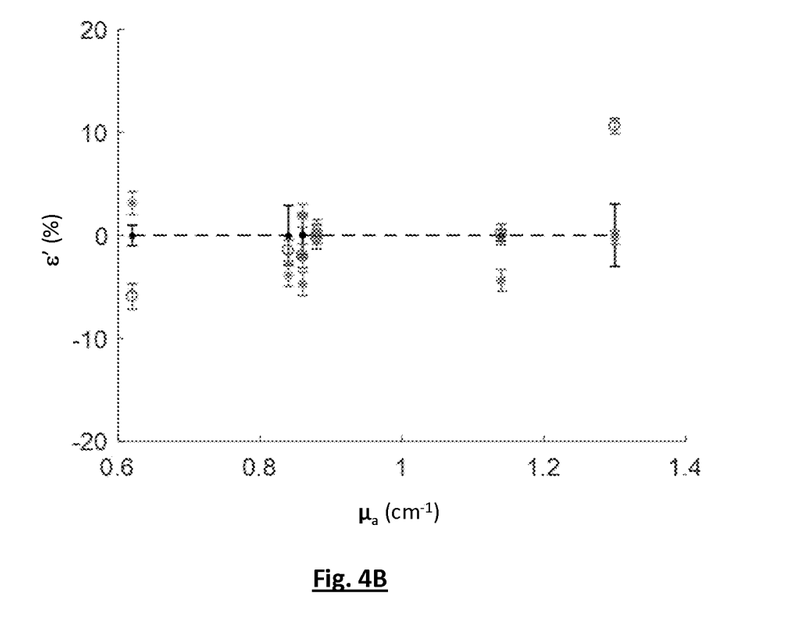
FIG. 4B shows a relative quantization error of a reduced scattering coefficient according to the absorption coefficient of the calibration sample.

FIG. 4B shows the relative error ε' affecting the determination of the reduced scattering coefficient $\mu_s'$ (ordinate axis) as a function of the actual absorption coefficient $\mu_a$ of each sample (abscissa axis). The points shown in FIG. 4B correspond to those of FIG. 4A.

It is observed that using the bundle of optical fibres 25 affords a significant increase in the performance of the contact configuration, the relative error associated with determining the scattering or absorption coefficients being less than ±5%. Performance levels close to those afforded by the remote configuration are thus obtained.

The invention could be used to study the absorption or scattering optical properties of objects, and in particular of biological tissues, for example the skin of a human or of another animal. The absorption or scattering optical properties may make it possible to quantify the presence of chromophore elements in tissues, or to carry out measurements for oximetry, which can be used for diagnosis or to follow up on the treatment of individuals. The invention may have applications in other industrial fields, for example in the agri-food industry.

The invention claimed is:

1. A Device for measuring radiation backscattered by a sample including:
   - at least one light source that is configured to emit a light beam, along an axis of incidence, towards a surface of the sample so as to form, on said surface, an elementary illumination zone;
   - an image sensor for forming an image of the radiation backscattered by the sample when the latter is illuminated by the light source, the image sensor lying in a detection plane;
   - a bundle of optical fibres, extending, along an extension axis, between a proximal surface and a distal surface, the proximal surface being applied against the image sensor, the distal surface being configured to be applied against the surface of the sample;

wherein the light source is arranged around the bundle of optical fibres, and wherein the distance between the light source and the bundle of optical fibres is less than 1 mm.

2. The device according to claim 1, wherein the light source is arranged around the bundle of optical fibres, between the image sensor and the sample.

3. The device according to claim 1, wherein the light source is flush with the distal surface.

4. The device according to claim 1, wherein the extension axis is perpendicular to the detection plane.

5. The device according to claim 1, wherein the optical fibres of the bundle of optical fibres:
   - are oriented in parallel to the extension axis;
   - or form a bundle diverging or converging away from/ toward the image sensor.

6. The device according to claim 1, including a plurality of light sources, each light source being arranged around the bundle of optical fibres.

7. The device according to claim 1, wherein at least two light sources emit light beams in different spectral bands, respectively.

8. The device according to claim 1, wherein at least one light source is such that the axis of incidence of the light beam produced by the latter intersects the extension axis of the bundle of optical fibres.

9. The device according to claim 1, wherein at least one light source is:
   - a light-emitting diode;
   - or a laser diode;
   - or an end of an illuminating optical fibre, the illuminating optical fibre being coupled to an illuminating source.

10. The device according to claim 1, wherein the image sensor, the bundle of optical fibres and each light source are held securely to one another by means of a holding support.

11. The device according to claim 1, wherein the image sensor includes a matrix-array of pixels, such that the distance, parallel to the detection plane, between at least the light source and the matrix-array of pixels is less than 1 mm or less than 500 µm.

12. A method for estimating a scattering and/or absorption optical property of a sample using a device according to claim 1, the method including:
   a) illuminating the sample using the light source of the device so as to form, on a surface of the sample, an elementary illumination zone;
   b) forming, using the image sensor, an image representing radiation backscattered by the sample under the effect of the illumination, the backscattered radiation emanating from the surface of the sample outside of the elementary illumination zone at several distances, referred to as backscattering distances, away from the elementary illumination zone;
   c) determining a scattering and/or absorption optical property according to an intensity of the backscattered radiation, at various backscattering distances, at least one backscattering distance being less than 1 mm or than 500 µm.

* * * * *

UNITED STATES PATENT AND TRADEMARK OFFICE
CERTIFICATE OF CORRECTION

PATENT NO. : 10,718,709 B2
APPLICATION NO. : 16/227458
DATED : July 21, 2020
INVENTOR(S) : Nils Petitdidier et al.

Page 1 of 1

It is certified that error appears in the above-identified patent and that said Letters Patent is hereby corrected as shown below:

On the Title Page

Item (73), the Assignee's name is incorrect. Item (73) should read:
-- (73) Assignee: Commissariat a l'energie atomique et aux energies alternatives, Paris (FR) --

Signed and Sealed this
Nineteenth Day of January, 2021

Andrei Iancu
*Director of the United States Patent and Trademark Office*